July 30, 1957 E. S. BOERNER Plant Pat. 1,625
ROSE PLANT
Filed Nov. 29, 1956
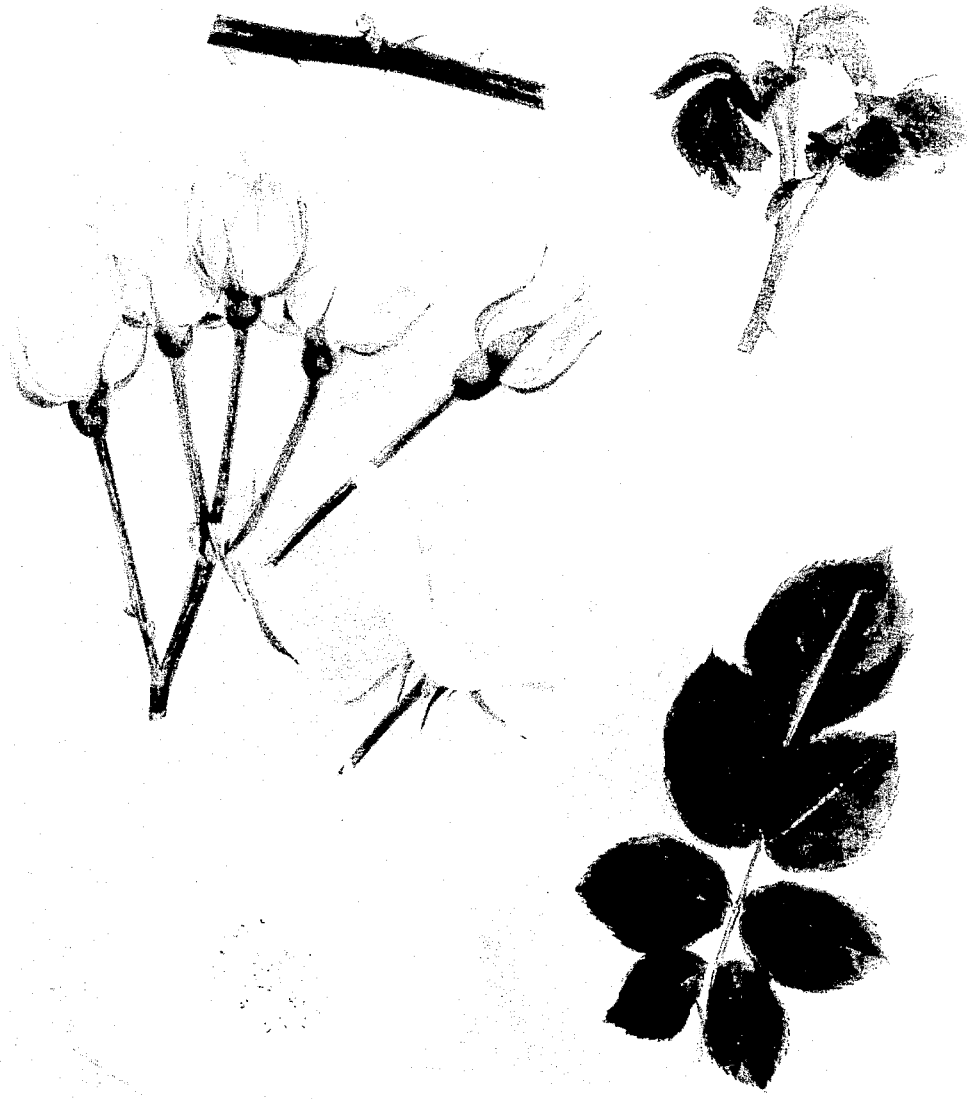
Inventor
E. S. Boerner
By: Robb & Robb
Attorneys.

United States Patent Office

Plant Pat. 1,625
Patented July 30, 1957

1,625

ROSE PLANT

Eugene S. Boerner, Newark, N. Y., assignor to Jackson & Perkins Company, Newark, N. Y., a corporation of New York Application November 29, 1956, Serial No. 625,203

1 Claim. (Cl. 47—61)

The present invention relates to a new and distinct variey of rose plant of the large-flowered polyantha class, which was originated by me by crossing an unnamed and unpatented seedling derived from a cross of "Pinocchio" (Plant Patent No. 484) × an unnamed and unpatented hybrid tea variety, with the variety "Fashion" (Plant Patent No. 789).

The primary objective of this breeding was to produce a new rose variety of the floribunda type which bears long-lasting flowers that are suitable for commercial cut flower use. This objective was fully achieved, along with other improvements, as evidenced by the following characteristics which are outstanding in the new variety and distinguish it from its parents, as well as from all other varieties of which I am aware:

(1) A vigorous and free-branching habit and continuous production of many flowers on each plant;

(2) The rich green foliage;

(3) The leathery and crisp flower petals which give the flowers a clean appearance throughout their life;

(4) The long-lasting quality of the flowers and their suitability for commercial cut flower use; and (5) The distinctive contrast between the light orange-yellow color of the flower stamens and the white, lightly overcast with La France Pink, general color tonality of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed seedling of "Pinocchio × an unnamed hybrid tea variety.

*Pollen parent.*—"Fashion."

Classification:

*Botanic.*—Large-flowered polyantha.

*Commercial.*—Floribunda.

*Flower*

(Observations made from specimens grown in a greenhouse at Newark, New York, in the early morning and in the latter part of May.)

Blooming habit: Recurrent—continuous.

Bud:

*Size.*—Medium.

*Form.*—Ovoid; is not affected by wet or hot weather.

*Color.*—When sepals first divide—Scarlet Red, Plate 1, lightly overcast with Rose Doree, Plate 1.

When petals begin to unfurl—Spinel Pink, Plate 26. When half-blown: inside of petals—Thulite Pink, Plate 26, lightly overcast with Rose Pink, Plate 12; reverse of petals—Thulite Pink, Plate 26.

*Sepals.*—Branched; curl back when petals begin to unfurl. Color: inside—Turtle Green, Plate 32; outside—Light Elm Green, Plate 27.

*Calyx.*—Color—Light Elm Green, Plate 27. Shape—pear. Size—small. Aspect—smooth. Odor when rubbed—none.

*Peduncle.*—Length—short. Aspect—rough. Strength—erect; slender. Color—Cedar Green, Plate 6.

*Opening.*—Opens up well; is not affected by adverse weather conditions.

Bloom:

*Size.*—Medium. Average size when fully expanded—3¼ inches.

*Borne.*—Both singly and in flat clusters.

*Stems.*—Medium length; strong.

*Form (when first open).*—Cupped. Permanence—flattens; outer petals curl back.

*Petalage.*—Double (full but open center). Number of petals under normal conditions—from 25 to 30.

*Color.*—Center of flower—White, Plate 53, lightly overcast with Hermosa Pink, Plate 1, and with an overcast of Marguerite Yellow, Plate 30, in the lower half of the petal. Outer petals—La France Pink, Plate 1. Base of petals (aiglet)—Barium Yellow, Plate 16. Inside of petals—White, Plate 53, lightly overcast with La France Pink, Plate 1, with outer edge of petal lightly overcast with Marguerite Yellow, Plate 30. Reverse of petals—Cameo Pink, Plate 26. General tonality from a distance—White, Plate 53, lightly overcast with La France Pink, Plate 1.

*Discoloration.*—General tonality at end of first day—White, Plate 53, lightly overcast with La France Pink, Plate 1. Second day—White, Plate 53, lightly overcast with La France Pink, Plate 1. Third day—White, Plate 53, lightly overcast with Hermosa Pink, Plate 1.

Petals:

*Texture.*—Leathery; crisp; is not affected by wet or hot weather.

*Appearance.*—Inside—satiny. Outside—shiny.

*Form.*—Oval; slightly notched.

*Arrangement.*—Imbricated (regularly arranged shingle-like).

*Petaloids in center.*—Few; small.

*Persistence.*—Drop off cleanly.

*Fragrance.*—Moderate. Nature—apple blossom.

*Lasting quality.*—On the plant—long. As cut flower—very long.

*Genital organs*

Stamens, anthers: Medium size; many; regularly arranged around styles. Color—Light Orange-Yellow, Plate 3.

Stamens, filaments (threads): Medium length. Color—Pinard Yellow, Plate 4.

Pollen: Color—Pale Yellow-Orange, Plate 3.

Styles: Bunched; uneven length; medium length; thin.

Stigmas: Color—Massicot Yellow, Plate 14.

Ovaries: All enclosed in calyx.

Hips: None.

Seeds: None.

*Plant*

Form: Bush.

Growth: Vigorous; upright; branching.

Foliage: Compound of 5 to 7 leaflets.

*Size.*—Medium.

*Quantity.*—Normal.

*Color.*—New foliage: upper side—Bordeaux, Plate 12, with mid-rib of Light Cress Green, Plate 31; under side—Kildare Green, Plate 31, lightly overcast with Oxblood Red, Plate 1. Old foliage: upper side—Forest Green, Plate 17; under side—Rainette Green, Plate 31.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; sharp.

*Leaf stem.*—Color—Light Cress Green, Plate 31. Under side—prickly.

*Stipules.*—Short; bearded.

Wood:

*New wood.*—Color—Absinthe Green, Plate 31. Bark—smooth.

*Old wood.*—Color—Elm Green, Plate 17. Bark—Smooth.

Thorns:

*Thorns.*—Quantity: on main stalks from base—ordinary; on laterals from stalk — ordinary.

Form—narrow base; short; hooked downward. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its vigorous and free-branching habit of growth and continuous production of many flowers on each plant, its rich green foliage, its leathery and crisp flower petals and the resultant clean appearance of the flowers throughout their life, the long-lasting quality of its flowers as cut flowers, and the distinctive contrast between the light orange-yellow flower stamens and the white, lightly overcast with La France Pink, general color tonality of its flowers.

No references cited.